United States Patent [19]

Khambay et al.

[11] Patent Number: 5,834,515

[45] Date of Patent: Nov. 10, 1998

[54] NAPHTHOQUINONE DERIVATIVES

[75] Inventors: Bhupinder Pall Singh Khambay, Southall; Duncan Batty, Slough, both of England; August Hermann Niemeyer Marich, Santiago, Chile; Matthew Robert Cahill, Harpeden, England

[73] Assignee: British Technology Group Limited, London, England

[21] Appl. No.: 501,000

[22] PCT Filed: Apr. 26, 1995

[86] PCT No.: PCT/GB95/00953

§ 371 Date: Aug. 9, 1995

§ 102(e) Date: Aug. 9, 1995

[87] PCT Pub. No.: WO95/32176

PCT Pub. Date: Nov. 30, 1995

[30] Foreign Application Priority Data

May 20, 1994 [GB] United Kingdom .................... 9410299

[51] Int. Cl.[6] .................................................... A61K 31/12
[52] U.S. Cl. ............................ 514/682; 552/298; 552/299
[58] Field of Search .................................... 552/298, 299; 514/682

[56] References Cited

U.S. PATENT DOCUMENTS

| | | | |
|---|---|---|---|
| 4,115,584 | 9/1978 | Bellina et al. ............................ | 552/298 |
| 4,970,328 | 11/1990 | Lindner et al. ........................... | 552/299 |
| 5,053,418 | 10/1991 | Latter et al. ............................. | 514/682 |
| 5,310,762 | 5/1994 | Latter et al. ............................. | 514/682 |

OTHER PUBLICATIONS

Cooke, Aust. J. of Scientific Research, vol. 3A, pp. 481–486 (1950).

*Primary Examiner*—James H. Reamer
*Attorney, Agent, or Firm*—Nixon & Vanderhye

[57] ABSTRACT

The invention relates to certain naphthoquinone derivatives, some of which are novel, of the general formula I (I)

in which R represents a hydrogen atom or a hydroxyl or an ethanoyloxy group; methods for their preparation; compositions containing such compounds and their use as pesticides, such as fungicides and, especially, insecticides and acaricides. Compounds of formula I may be derived from plants of the genus Calceolaria and the invention therefore also relates to extracts of a Calceolaria species and their use as pesticides.

16 Claims, No Drawings

NAPHTHOQUINONE DERIVATIVES

This invention relates to certain naphthoquinone derivatives, one of which is novel, methods for their preparation, compositions containing such compounds and their use as pesticides, such as fungicides and, especially, insecticides and acaricides.

It has been found that extracts of plants of the genus Calceolaria, particularly *Calceolaria sessilis, Calceolaria andina* and *Calceolaria glabrata var. meyenenis* found in Chile, exhibit pesticidal activity. Purification and analysis of these extracts has resulted in the isolation and identification of certain naphthoquinone derivatives which also exhibit pesticidal activity.

According to the present invention there is therefore provided a compound of general formula I

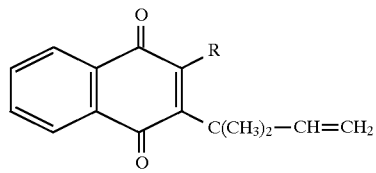

in which R represents a hydrogen atom or a hydroxyl or an ethanoyloxy group, for use as a pesticide, for instance, a fingicide and/or, especially, an insecticide and/or an acaricide.

The compound of formula I may be in pure form or in admixture with one or more other compounds of formula I. It is particularly preferred that the compound of formula I, or at least one of the compounds of formula I, is that in which R represents an ethanoyloxy group.

The compound of formula I in which R represents a hydroxyl group may tautomerise to form the corresponding 4hydroxynaphthalene-1,2-dione and the invention therefore also includes this tautomer. In addition, the compound of formula I in which R represents a hydroxyl group may form salts with alkali metals, such as sodium and potassium, and alkaline earth metals and these salts also form part of the invention.

As mentioned above, extracts of plants of the genus Calceolaria are themselves pesticidally active. Thus, according to another aspect of the present invention there is provided an extract of a Calceolaria species for use as a pesticide, for instance, a fungicide and/or, especially, an insecticide and/or an acaricide.

A partially purified extract of a Calceolaria species may be employed. Preferably, the extract comprises at least one compound of formula I as defined above.

Compounds of formula I or extracts as defined above may be obtained by extracting comminuted plant material, for instance, the leaves and/or stems, of a Calceolaria species with a solvent. Initial extraction is preferably carried out with a hydrocarbon solvent such as an alkane, especially hexane, the extract then being concentrated, for instance, by evaporation. The concentrated extract may then be purified by chromatography, suitably column chromatography using a silica gel column, followed by further separation processes.

Preferably, the Calceolaria species is *Calceolaria andina, Calceolaria sessilis* or *Calceolaria glabrata var. meyenenis.*

The compounds of formula I may be utilised as a pesticide in the form of an extract as defined above. Alternatively, the isolated compounds of formula I or extracts of a Calceolaria species may be formulated with an inert carrier or diluent to produce a pesticidal composition. According to a further aspect of the present invention there is therefore provided a pesticidal, for instance, a fungicidal and/or, especially, an insecticidal and/or acaricidal, composition which comprises a carrier and, as active ingredient, a compound of formula I as defined above or an extract of a Calceolaria species as defined above.

The compositions of the invention may contain from 0.001 to 95% by weight of the active ingredient of formula I. Preferably, the compositions contain from 0.001 to 25% by weight of the active ingredient when they are in ready-to-use form. However, higher concentrations, for instance, up to 95%, may be present in compositions to be sold as concentrates for dilution before use.

The compositions of the invention may be mixed with a variety of appropriate inert carriers such as solvents, diluents and/or surface-active agents to form dusts, granular solids, wettable powders, mosquito coils or other solid preparations or emulsions, emulsifiable concentrates, sprays, aerosols or other liquid preparations. Suitable solvents and diluents include water, aliphatic and aromatic hydrocarbons such as xylene or other petroleum fractions and alcohols such as ethanol. Surface-active agents may be of an anionic, cationic or non-ionic type. Anti-oxidants or other stabilisers may also be included as well as perfumes and colourings. These inert carriers may be of the type and in proportions such as are conventionally used in pesticidal compositions.

In addition to these inert carriers, the compositions of the invention may also contain one or more further active ingredients. These further active ingredients may be other compounds which exhibit pesticidal activity and these other compounds may exhibit a synergistic effect with the compounds of the present invention.

Compounds of formula I and extracts of a Calceolaria species as defined above may be used to control pest infestation in domestic, horticultural, agricultural, medical or veterinary environments. Thus, according to another aspect of the present invention there is provided the use as a pesticide, for instance, a fungicide and/or, especially, an insecticide and/or acaricide, of a compound of formula I as defined above, an extract of a Calceolaria species as defined above or a composition as defined above.

The present invention also provides a method of combating pests, such as fungi and/or, especially, insects and/or acarids, at a locus which comprises treating the locus with a compound of formula I as defined above, an extract of a Calceolaria species as defined above or a composition as defined above. Preferably, the locus comprises the pests per se or environments subject to or subjected to attack by pests. More preferably, the locus comprises the pests per se, stored food material, plants or animals subject to or subjected to attack by pests, seeds of such plants or the medium in which such plants are growing or are to be grown. Specifically, compounds of formula I, extracts and compositions as defined above may be used in a domestic environment for spraying rooms to combat infestation by houseflies or other insects, in a horticultural or agricultural environment for treatment of stored crops, especially cereals, or to spray growing crops such as cotton or rice to combat infestation by fingi, insects or other pests, and in a medical or veterinary environment, for instance, as a cattle spray to prevent or treat infestation by insects or other pests.

The synthesis of the compound of formula I in which R represents a hydroxyl group is disclosed by R. G. Cooke in Aust. J. Sci. Res., (1950), pp 481–486 and the $^{13}$C NMR spectrum of this compound is disclosed by I. A. McDonald, T. J. Simpson and A. F. Sierakowski in Aust. J. Chem., (1977), 30, pp 1727–34.

In addition, the isolation of compounds of formula I in which R represents a hydroxyl or ethanoyloxy group from the aerial parts of *Calceolaria sessilis* and the physical characterisation of these compounds is described by M. C. Chamy, I. Jimenez, M. Piovano, J. A. Garbarino and B. Didyk in Biol. Sec. Chil. Quim. (1993), 38, pp 187–190. However, the remaining compounds of formula I would appear to be novel. According to a further aspect of the present invention there is therefore provided a compound of general formula I as defined above in which R represents a hydrogen atom or an ethanoyloxy group.

The compound of formula I in which R represents an ethanoyloxy group may be prepared by reacting the compound of formula I in which R represents a hydroxyl group with an ethanoyl halide, especially ethanoyl chloride. Preferably, the reaction is carried out in the presence of a solvent. Suitable solvents include chlorinated hydrocarbons, such as dichloromethane, aromatic and heteroaromatic compounds, such as pyridine, and mixtures thereof. It is also preferred that the reaction is carried out at a temperature in the range from 0° C. to 40° C., more preferably 15° to 30° C., with ambient temperatures (about 20° C.) being especially preferred.

The compound of formula I in which R represents a hydroxyl group may be prepared by refluxing 2-(3-methylbut-2-enyloxy)naphthalene-1,4-dione in an alcohol, preferably absolute ethanol.

2-(3-Methylbut-2-enyloxy)naphthalene-1,4-dione may be prepared by reacting 2-hydroxynaphthalene-1,4-dione with triphenylphosphine and diethyl azodicarboxylate followed by 3-methylbut-2-enol in the presence of a solvent, such as tetrahydrofuran.

2-Hydroxynaphthalene-1,4-dione (otherwise known as Lawsone or Henna) is a known compound which is commercially available.

The invention is further illustrated by the following examples.

EXAMPLE 1

Extraction Procedure

Comminuted plant material (450 g) of *Calceolaria andina* from Chile were extracted with hexane (2×1500 ml) using microwave irradiation (Panasonic NN-6452B, 800 W, 3 minutes). The combined extracts were evaporated to dryness under reduced pressure to yield a green oil (10.8 g) (Extract A).

The residue was eluted under suction from silica gel (Silica Gel 60H, Merck 7736) with a mixture of petrol and ether (2:1), to give two active fractions, which were then combined (4.79 g).

The combined active fractions were eluted from silica gel (Silica Gel 60, Merck 9385) with a mixture of petrol and ether (4:1). The major components were combined and evaporated to dryness (3.81 g).

The major components (1.76 g) were dissolved in ether (50 ml) and extracted with saturated aqueous sodium carbonate solution (4×50 ml).

The combined basic fractions were acidified to pH 5 with 2M hydrochloric acid and extracted with ether (3×40 ml). The combined ether extracts were washed with water (2×25 ml), saturated aqueous sodium chloride solution (25 ml) and dried over magnesium sulphate. Filtration and evaporation of the solvent under reduced pressure yielded a red solid (226 mg), m.p. 60° C., identified by NMR as the compound of formula I in which R represents a hydroxyl group (Compound B).

The remaining organic layer was washed with saturated aqueous sodium chloride solution (25 ml) and dried over magnesium sulphate. Filtration and evaporation yielded a reddish solid (1.53 g).

The reddish solid (1.50 g) was eluted from silica gel (Silica Gel 60, Merck 7736) using a mixture of petrol and ether (4:1) and two compounds were isolated. The less polar compound (48 mg) was identified as the compound of formula I in which R represents a hydrogen atom (Compound A) whilst the second, more polar compound (1.14 g), m.p. 55° C., was identified as the compound of formula I in which R represents an ethanoyloxy group (Compound C).

The $^1$H NMR and $^{13}$C NMR spectra (obtained for a solution in CDCl$_3$, using tetramethylsilane as internal standard, on a JEOL GX400 spectrometer at 400 MHz for $^1$H NMR and 100 MHz for $^{13}$C NMR) showed peaks as set out in Table 1 below:

TABLE 1

(structure of formula I: naphthalene-1,4-dione with substituent R at position 2 and C(CH$_3$)$_2$—CH=CH$_2$ at position 3; carbons numbered 1–15, with 11, 14/15, 12, 13 on the side chain)

| No. assigned to carbon atom (see formula) | Compound A (R = H) $^1$H | δ ppm $^{13}$C |
|---|---|---|
| 1 | — | 184.5 |
| 2 | 6.89 (s) | 134.4 |
| 3 | — | 156.7 |
| 4 | — | 185.8 |
| 5 | 8.02–8.05 (m) | 125.6 |
| 6 | 7.68–7.74 (m) | 133.8 |
| 7 | 7.68–7.74 (m) | 133.4 |
| 8 | 8.05–8.07 (m) | 126.9 |
| 9 | — | 131.5 |
| 10 | — | 133.3 |
| 11 | — | 41.0 |
| 12 | 6.18(dd, 17.3, 10.4) | 145.4 |
| 13 | 5.08(d, 10.4) 5.05(d, 17.3) | 112.7 |
| 14 | 1.46 (s) | 27.1 |
| 15 | 1.46 (s) | 27.1 |
| 16 | — | — |
| 17 | — | — |

| No. assigned to carbon atom (see formula) | Compound B (R = OH) $^1$H | δ ppm $^{13}$C |
|---|---|---|
| 1 | — | 182.2 |
| 2 | (OH) 7.89 (s) | 152.9 |
| 3 | — | 128.4 |
| 4 | — | 184.8 |
| 5 | 8.05(d, 7.6) | 127.0 |
| 6 | 7.74(dt, 1.2, 7.6) | 135.2 |
| 7 | 7.65(dt, 1.2, 7.6) | 132.6 |
| 8 | 8.03(d, 7.6) | 125.8 |
| 9 | — | 128.2 |
| 10 | — | 134.1 |
| 11 | — | 41.0 |
| 12 | 6.29(dd, 17.4, 10.4) | 148.1 |
| 13 | 4.96(d, 10.4) 4.98(d, 17.4) | 109.6 |
| 14 | 1.57 (s) | 28.1 |
| 15 | 1.57 (s) | 28.1 |
| 16 | — | — |
| 17 | — | — |

| No. assigned to carbon atom (see formula) | Compound C (R = OC$^{16}$OC$^{17}$H$_3$) $^1$H | δ ppm $^{13}$C |
|---|---|---|
| 1 | — | 178.6 |
| 2 | — | 150.7 |

TABLE 1-continued

| | | |
|---|---|---|
| 3 | — | 143.9 |
| 4 | — | 185.1 |
| 5 | 8.03(d, 7.0) | 126.8[b] |
| 6 | 7.73(dt, 1.2, 7.0) | 134.3[c] |
| 7 | 7.69(dt, 1.2, 7.0) | 133.4[c] |
| 8 | 8.03(d, 7.0) | 126.1[b] |
| 9 | — | 133.4[a] |
| 10 | — | 133.0[a] |
| 11 | — | 41.5 |
| 12 | 6.19(dd, 17.4, 10.4) | 147.2 |
| 13 | 4.99(d, 10.4) | 109.5 |
| | 4.96(d, 17.4) | |
| 14 | 1.53 (s) | 27.6 |
| 15 | 1.53 (s) | 27.6 |
| 16 | | 168.3 |
| 17 | 2.32 (s) | 20.7 |

Assignments marked a, b, c are interchangeable
s = singlet, d = doublet, dd = double doublet, dt = double triplet, m = multiplet
Figures in parentheses are coupling constants (J) in Hz EXAMPLE 2
Alternative Extraction Procedure Comminuted plant material (100 g) of Calceolaria andina were stood in hexane (500 ml) for 2 hours before stirring for 10 minutes. The solvent was filtered and the residue extracted further with hexane (2×500 ml). The combined hexane extracts were evaporated to dryness to give a green solid (2.23 g) (Extract B). This was separated as described in Example 1.

EXAMPLE 3
Preparation of 2-(1,1-dimethylprop-2-enyl)-3-hydroxynaphthalene-1,4-dione (Compound B. Formula I: R=—OH)
(i) Preparation of 2-(3-methylbut-2-enyloxy)naphthalene-1,4-dione To a stirred solution of 2-hydroxynaphthalene-1,4-dione (10.0 g, 57.4 mmol) and triphenylphosphine (15.1 g, 57.4 mmol) in dry tetrahydrofuran (150 ml) at 0° C. under an atmosphere of nitrogen was added diethyl azodicarboxylate (10.0 g, 57.4 mmol). After stirring for a further 5 minutes, a solution of 3-methylbut-2-enol (7.42 g, 86.1 mmol) in dry tetrahydrofuran (10 ml) was added dropwise and stirring was continued for 2 hours. The precipitate was collected, air-dried and recrystallised from aqueous methanol to yield the title compound (8.3 g) as a yellow crystalline solid with a melting point of 138° C.

$^1$H NMR (400 MHz) d 1.76 (s, 3H, 3 x H-15), 1.81 (s, 3H, 3×H-14), 4.59 (d, 2H, J=6.9 Hz, 2×H-11), 5.49 (t, H, J =6.9 Hz, H-12), 6.16 (s, H-3), 7.68–7.76 (m, 2H, H-6 and H-7), 8.06–8.13 (m, 2H, H-5 and H-8).

$^{13}$C NMR (100 MHz) d 18.4 (15), 25.8 (14), 66.4 (11), 110.5 (3), 117.2 (12), 126.1$^a$ (5), 126.7$^a$ (8), 131.1$^b$ (9), 132.0$^b$ (10), 133.2$^c$ (7), 134.2$^c$ (6), 140.5 (13), 159.5 (2), 180.3 (1) and 185.0 (4)
where a, b or c are interchangeable assignments.

(ii) Preparation of 2-(1,1-dimethylprop-2-enyl)-3-hydroxynaphthalene- 1,4-dione

A solution of 2-(3-methylbut-2-enyloxy)naphthalene-1,4-dione (4.27 g, 24.8 mmol) obtained in (i) above in absolute ethanol (125 ml) was refluxed for 6 hours. The mixture was cooled and the solvent removed in vacuo. The residue was dissolved in diethyl ether and extracted with 1% (w/v) aqueous sodium hydroxide solution (6×25 ml). The combined basic fractions were acidified to pH 5 with 2M hydrochloric acid and extracted with diethyl ether (6×25 ml). The combined ethereal extracts were washed successively with water (2×25 ml), saturated aqueous sodium chloride solution (25 ml) and dried over anhydrous magnesium sulphate. Filtration and evaporation of the solvent under reduced pressure followed by recrystallisation from aqueous methanol, yielded the title compound (4.27 g) as a yellow crystalline solid, m.p. 60° C.

EXAMPLE 4
Preparation of 2-(1,1-dimethylprop-2-enyl)-3-ethanoyloxynaphthalene-1,4-dione (Compound C, Formula I: R=—O—CO—CH$_3$)

To a stirred solution of 2-(1,1-dimethylprop-2-enyl)-3-hydroxy-naphthalene-1,4-dione (20.0 g, 82.6 mmol) obtained as in Example 3 above in a mixture of dry dichloromethane (250 ml) and pyridine (50 ml) at 0° C. was slowly added a solution of ethanoyl chloride (25.9 g, 330 mmol) in dichloromethane (25 ml) over 40 minutes. The stirred mixture was slowly allowed to warm to room temperature over 2 hours before washing successively with water (50 ml), 2M hydrochloric acid (2×50 ml), water (2×50 ml), saturated aqueous sodium carbonate solution (2×50 ml), water (2×50 ml), saturated aqueous sodium chloride solution (50 ml) and drying over magnesium sulphate. Filtration and evaporation of the solvent under reduced pressure and recrystallisation from aqueous methanol yielded the title compound (21.6 g) as a yellow crystalline solid, m.p. 55° C.

EXAMPLE 5
Pesticidal Activity

Pesticidal activity was assessed against houseflies, mustard beetles, diamond-back moths, mites and whitefly using the following methods.

Houseflies (MD) (*Musca domestica*)

Female flies were treated on the thorax with a one microlitre drop of test compound dissolved in acetone. Two replicates of 15 flies were used at each dose rate and 6 dose rates were used per compound under test. After treatment, the flies were maintained at a. temperature of 20°±1° C. and kill was assessed 24 and 48 hours after treatment. LD$_{50}$ values were calculated in micrograms of test compound per fly (see Sawicki et al, Bulletin of the World Health Organisation, 35, 893, (1966) and Sawicki et al, Entomologia and Exp. Appli 10, 253, (1967).

Mustard beetles (PC) (*Phaedon cochleariae fab*)

A one microlitre drop of an acetone solution of the test compound was applied ventrally to adult mustard beetles using a micro drop applicator. The treated insects were maintained for 48 hours after which time kill was assessed. Two replicates each of 20 to 25 mustard beetles were used at each dose level and 5 dose levels were treated comparably. LD$_{50}$ values were calculated as for houseflies.

Diamond-back moth (PX) (*Plutella xylostella*)

Fifth instar larvae were treated with a 0.5 μl drop of test compound in acetone. Three replicates of 10 larvae each were used at each dose rate and 5 dose rates were used per compound under test. After treatment, the larvae were maintained at about 22° C., and kill was assessed as failure to pupate 5 days later. LD$_{50}$ values were calculated as for houseflies.

Mites (TU) (*Tetranychus urticae*)

25 adult female mites were immersed in 35 μl of a solution of the test compound in a 1:4 acetone-water mixture for 30 seconds. The treated insects were maintained at 21°±2° C. and kill was assessed 72 hours after treatment. Mites exhibiting repetitive (non-reflex) movement of more than one locomotory appendage after this period were recorded as alive. Three replicates of 25 mites each were used at each dose rate and 5 or 6 dose rates were used per compound under test. $LC_{50}$ values were calculated in ppm of the solution of the test compound per insect The test was carried out using three different strains of mites, one susceptible (GSS) and the others (NYR-Bif-1000 and UK-S-Carb-600) resistant to bifenthrin and carbaryl respectively. The GSS strain was supplied by Schering, AG, Berlin. The NYR-Bif-1000 strain was provided by the Department of Entomology, Cornell University, New York, having subjected a field strain to selection with bifenthrin. The UK-S-Carb-600 strain was obtained by applying selection with carbaryl to the UK-S strain provided by Shell Research Limited, Sittingbourne. (See T. J. Dennehy, A. W. Farnham and I. Denholm, Pestic. Sc., 39, 47–54, (1993).

Whitefly (BT) (*Bemisia tabaci*)

Acetone solutions (0.100 ml) of the test compounds were placed in 10 ml glass vials and evaporated with rotation to deposit a film of the compound. Thirty adult whiteflies were placed inside the vial, then after 60 minutes, the treated insects were transferred onto untreated cotton leaf discs which were kept moist on a bed of agar gel. The temperature was maintained at 25° C. and mortality assessed after 48 hours. Three replicates were used at each of 5 to 7 dose levels per compound. $LC_{50}$ values were calculated by using a computer software package ("Polo-PC" available from LeOra Software, Berkeley, Calif.). (See M. W. Cahill and B. Hackett in Proceedings Brighton Crop Protection Conference, 1992). The test was carried out using three different strains of whitefly, one susceptible and two resistant to pyrethroid insecticides. The susceptible strain (SUD-S) was collected in Sudan in 1978 from cotton, one resistant strain (Ned 3) was collected in the Netherlands in 1992 from gerbera and the other resistant strain (USA-B) was collected in Southern USA in 1985 from poinsettia).

The results of these tests are set out in Tables 2 and 3 below. The values given are $LD_{50}$ (μg/insect) or $LC_{50}$ (ppm solution of test compound) unless otherwise specified.

TABLE 2

| Pest | Compound A (R = H) | Compound B (R = —OH) | Compound C (R = —O—CO—CH$_3$) |
|---|---|---|---|
| MD | 4%* | 1.8 μg | 5.3 μg |
| PC | 25%* | c. 3.0 μg | c. 6.0 mg |
| PX | 30%** | 30%** | 20%** |
| TU (GSS) | | 85 ppm | 74 ppm |
| TU (NYR-Bif-1000) | | 110 ppm | 120 ppm |
| TU (UK-S-Carb-600) | | 64 ppm | 135 ppm |
| BT (SUD-S) | | 42 ppm | 3.6 ppm |
| BT (Ned 3) | | 14 ppm | 5.5 ppm |
| BT (USA-B) | | 34 ppm*** | 11 ppm*** |

*% kill at 20 μg/insect
**% kill at 10 μg/insect
***mortality assessed at 24 hours instead of 48 hours.

TABLE 3

| Pest | Extract A (Example 1) | Extract B (Example 2) |
|---|---|---|
| MD | 28%* | 7%* |
| PC | 30%* | 40%* |
| PX | | 25%** |
| TU (GSS) | c. 100 ppm | c. 130 ppm |

*% kill at 20 μg insect
**% kill at 10 μg insect

EXAMPLE 6

Activity against whitefly (TV) (*Trialeurodes vaporariorum*)

A leaf disc was submerged in a 40% acetone:water solution of Compound C and then left to dry. Adult whiteflies were then confined in a Petri dish with the treated leaf Four replicates of 10 adult whitefly were used for each dose rate. Kill was assessed at specified times were treatment and percentage mortalities, corrected using Abbott's formula, were calculated.

The results of this test are given in Table 4 below.

TABLE 4

| Concentration of Compound C (ppm) | % mortality | |
|---|---|---|
| | 24 hours | 48 hours |
| 1000 | 100 | 100 |
| 100 | 79 | 100 |
| 10 | 0 | 0 |
| 1 | 0 | 0 |

These results indicate an $LC_{50}$ of 10–100 ppm for Compound C against this insect.

Tests have also shown that the compounds of formula 1 exhibit aphicidal activity against various species of aphid, especially *Myzus persicae* and *Aphis gossypii*.

In addition, tests have shown that the compounds of formula I exhibit good fungicidal activity against a broad spectrum of fungi which cause diseases in both cereal and broad-leaved crops. Particularly good activity has been observed against fungi of the genera Erysiphe, especially *Erysiphe graminis*, Botrytis especially *Botrytis fabae* and *Botrytis cinerea*, Rhizoctonia, especially *Rhizoctonia solani* and *Rhizoctonia cerealis*, Pyricularia, expecially *Pyricularia oryzae* and Aspergillus, especially *Aspergillus niger*.

We claim:

1. A method of combating pests at a locus which comprises treating the locus with a compound of the formula (I)

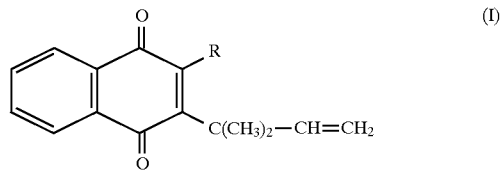

in which R represents a hydrogen atom, an ethanoyloxy group or a hydroxyl group or salt thereof.

2. A method according to claim 1, which R represents a hydroxyl or ethanoyloxy group.

3. A method of combating pests at a locus, which comprises treating the locus with an extract of plant material from a Calceolaria species, wherein the extract comprises at least one compound of formula I as defined in claim 1.

4. A method according to claim 3, wherein the extract is obtainable by extracting comminuted plant material of a Calceolaria species with a solvent.

5. A method according to claim 3, wherein the extract is obtainable by extracting comminuted plant material of *Calceolaria andina* with hexane.

6. A extract of plant material from a Calceolaria species in which the Calceolaria species is *Calceolaria andina*, *Calceolaria sessilis* or *Calceolaria glabrata var. meyenenis* obtainable by extracting the comminuted material with hexane.

7. A extract obtainable by concentrating an extract of claim 6.

8. A pesticidal composition which comprises a carrier and, as active ingredient, a compound of formula I according to claim 1.

9. A pesticidal composition which comprises a carrier and, as a active ingredient, a compound as defined in claim 2.

10. A pesticidal composition which comprises a carrier and, as. active ingredient, an extract according to claim 6.

11. A pesticidal composition which comprises a carrier and, as active ingredient, an extract according to claim 7.

12. A composition according to claim 8 comprising an inert carrier selected from solvents, diluents and/or surface active agents.

13. A composition according to claim 9 comprising an inert carrier selected from solvents, diluents and/or surface active agents.

14. A composition according to claim 10 comprising an inert carrier selected from solvents, diluents and/or surface active agents.

15. A composition according to claim 11 comprising an inert carrier selected from solvents, diluents and/or surface active agents.

16. A compound of general formula I as defined in claim 6 in which R represents a hydrogen atom.

* * * * *